US012699082B2

(12) United States Patent
Lim et al.

(10) Patent No.: US 12,699,082 B2
(45) Date of Patent: Aug. 4, 2026

(54) METHOD FOR CONSTRUCTION OF PANCREATIC CANCER ORGANOID

(71) Applicant: Yonsei University BioHealth Technology Holdings, Inc., Seoul (KR)

(72) Inventors: Jong Baeck Lim, Seoul (KR); Jae Il Choi, Seoul (KR); Joon Seong Park, Gyeonggi-do (KR); Sung Ill Jang, Seoul (KR); Jae Hee Cho, Seoul (KR)

(73) Assignee: Yonsei University BioHealth Technology Holdings, Inc., Seoul (KR)

( * ) Notice: Subject to any disclaimer, the term of this patent is extended or adjusted under 35 U.S.C. 154(b) by 670 days.

(21) Appl. No.: 18/040,849

(22) PCT Filed: Aug. 6, 2021

(86) PCT No.: PCT/KR2021/010382
§ 371 (c)(1),
(2) Date: Feb. 7, 2023

(87) PCT Pub. No.: WO2022/031095
PCT Pub. Date: Feb. 10, 2022

(65) Prior Publication Data
US 2023/0296585 A1      Sep. 21, 2023

(30) Foreign Application Priority Data
Aug. 7, 2020      (KR) ........................ 10-2020-0099077

(51) Int. Cl.
*G01N 33/50*          (2006.01)
*C12N 5/09*           (2010.01)

(52) U.S. Cl.
CPC ....... *G01N 33/5011* (2013.01); *C12N 5/0693* (2013.01); *G01N 33/5082* (2013.01); (Continued)

(58) Field of Classification Search
None
See application file for complete search history.

(56) References Cited

U.S. PATENT DOCUMENTS

| | | | |
|---|---|---|---|
| 2017/0285002 A1 | 10/2017 | Taniguchi | |
| 2019/0376043 A1* | 12/2019 | Lee | A01K 67/0275 |
| 2019/0390149 A1 | 12/2019 | Cho | |

FOREIGN PATENT DOCUMENTS

CN          110317790 B   *  5/2021   ........... C12N 5/0693

OTHER PUBLICATIONS

Choi, Jae-Il; et al; "Cancer-initiating cells in human pancreatic cancer organoids are maintained by interactions with endothelial cells" Cancer Letters, 498, 42-53, 2021 (Year: 2021).*

(Continued)

*Primary Examiner* — David W Berke-Schlessel
(74) *Attorney, Agent, or Firm* — McDonnell Boehnen Hulbert & Berghoff LLP

(57)            ABSTRACT
Pancreatic cancer organoids prepared by a method of the present invention sufficiently reflect the interaction between cancer cells and endothelial cells, that is, cross-talk with the vascular niche, and thus they can show the characteristics of cancer-initiating cells (CICs) present in the organism environment, compared to conventional cancer organoids. Accordingly, the clinical applicability and reliability of the screened drug may be further remarkably increased.

7 Claims, 12 Drawing Sheets

(52) U.S. Cl.
CPC .... *C12N 2501/11* (2013.01); *C12N 2501/415* (2013.01); *C12N 2513/00* (2013.01); *C12N 2533/90* (2013.01)

(56) References Cited

OTHER PUBLICATIONS

Lazzari, Gianpiero; et al; "Multicellular spheroid based on a triple co-culture: A novel 3D model to mimic pancreatic tumor complexity" Acta Biomaterialia, 78, 296-307, 2018 (Year: 2018).*

C.M. Cattaneo et al., "Tumor organoid-T-cell coculture systems," Nature Protocols, 15, 15-39 (2020).

K. Klimkiewicz et al., "A 3D model of tumour angiogenic microenvironment to monitor hypoxia effects on cell interactions and cancer cell selection," Cancer Letters, 396, 10-20 (2017).

G. Lazzari et al., "Multicellular spheroid based on a triple co-culture: A novel 3D model to mimic pancreatic tumor complexity," Acta Biomaterialia, 78, 296-307 (2018).

International Search Report (translation) and Written Opinion (with machine translation) PCT/KR2021/010382, dated Nov. 18, 2021.

Lai Benjamin et al., Recapitulating pancreataic tumor microenvironment through synergistic use of patient rganoids and organ-on-a-chip vasculature, Adv Funct Mater. (2020) 30(48).

* cited by examiner

Human pancreatic cancer organoid

METHOD FOR CONSTRUCTION OF PANCREATIC CANCER ORGANOID

CROSS-REFERENCE TO RELATED APPLICATIONS

This application is a U.S. National Stage application of International Patent Application no. PCT/KR2021/010382, filed Aug. 6, 2020, which claims the benefit of priority of Korean Patent Application no. 10-2020-0099077, filed Aug. 7, 2020.

TECHNICAL FIELD

The present invention relates to a method for preparing pancreatic cancer organoids, and more specifically, the present invention relates to pancreatic cancer organoids prepared by co-culture with endothelial cells or using an endothelial cell conditioned medium so as to contain cancer-initiating cells.

BACKGROUND ART

Among a total of 65,479 people who died of diseases in 2005, 26.7% of the total deaths were due to cancers. Among these cancers, pancreatic cancer in particular has a very poor prognosis, and shows a 5-year survival rate of less than 10% as reported by the National Cancer Institute. Although surgical excision can be performed for the treatment of such pancreatic cancer, there is a limitation in that only 15% of newly diagnosed patients are capable of undergoing such surgery.

Meanwhile, due to the aging population, the number of cancer patients in Korea and foreign countries rapidly increased, and thus studies have been actively conducted to overcome cancer through patient-specific anticancer therapy. In particular, in the case of targeted therapy, the treatment efficiency of anticancer drugs for terminal cancer patients can be significantly increased, and thus the side effects of the anticancer drugs can be minimized. In addition, the responsiveness of cancer cells to therapeutic agents can be predicted through cell signaling. In these terms, the clinical usefulness of targeted therapy is very high.

However, in the case of cancer cell lines prepared from primary patient samples, there are limitations in that not only it is very inefficient to establish cell lines from patient samples, but also genetic mutations occur in cell lines during the process of adaptation to two-dimensional culture and selection, resulting in loss of genetic heterogeneity. Furthermore, in the case of the cancer cell lines, there is also a limitation that other matrix components in tissues that can be used as standard are lacking.

Histoculture drug response assay (HRDA), which can test the sensitivity of patients to anticancer drugs in the preclinical stages, has limitations in that it is difficult to confirm sensitivity to various anticancer drugs because only a small amount of tissue is used, and the loss of major cancer tissue is great because the test can be performed only once.

In addition, a method of transplanting cancer cell lines or cancer cells derived from cancer patients into an animal model (patient-derived tumor xenograft, PDTX) has an advantage over cell-based models in that it better mimics the biological characteristics of tumor tissues, but has limitations in that it incurs a lot of cost, time and resources and poses issues associated with bioethics. In addition, some cancer organoids have limitations in that they lack immune components, vascular components, or cancer support cells including normal epithelial cells, and thus cannot sufficiently support clinical results.

In order to overcome these limitations, organoids (ex vivo tissue constructs) prepared by culturing or recombining cells isolated from stem cells or organ cells have been developed. Such organoids have an advantage in that a test treatment is first performed on the organoid on behalf of a patient, and based on the results of the test, an anticancer drug showing a useful therapeutic effect can be selected for each individual patient. However, conventional methods have a limitation that the success rate of preparation of the constructs is very low.

DISCLOSURE

Technical Problem

An object of the present invention is to provide a method for preparing pancreatic cancer organoids, and pancreatic cancer organoids prepared by the preparation method.

Another object of the present invention is to provide a method of screening a therapeutic agent for pancreatic cancer using the pancreatic cancer organoid according to the present invention.

However, objects to be achieved by the present invention are not limited to the above-mentioned objects, and other objects not mentioned herein will be clearly understood by those skilled in the art from the following description.

Technical Solution

One embodiment of the present invention provides a method for preparing pancreatic cancer organoids.

The preparation method of the present invention comprises steps of: a) dissociating a biological sample isolated from a pancreatic cancer patient and immobilizing the dissociated biological sample on Matrigel; b) forming pancreatic cancer organoids by culturing the sample immobilized on Matrigel in step a); c) dissociating the pancreatic cancer organoids formed in step b); and d) co-culturing the dissociated pancreatic cancer organoids with endothelial cells, or adding an endothelial cell conditioned medium to the dissociated pancreatic cancer organoids, followed by culture.

The "pancreatic cancer" in the present invention is divided into exocrine tumors and neuroendocrine tumors, and most types of pancreatic cancer are exocrine tumors corresponding to pancreatic ductal adenocarcinomas (PDACs). Cancer cells or tissues in such PDAC patients have a subpopulation of cells having chemoresistance and the capacity to self-renew and differentiate, which are cancer-initiating cells having phenotypes of CD44(+)CD24(+) and CD44(+)CD24(+)EpCAM(+), and thus the cancer cells in the PDAC patients are characterized by mostly metastasizing and being highly resistant to conventional therapies such as chemotherapy, radiotherapy and immune therapy. In particular, patients with cells having a CD44(+)CD24(+) phenotype have a very poor prognosis compared to patients without these cells. For the purposes of the present invention, the pancreatic cancer may be pancreatic ductal adenocarcinoma, without being limited thereto.

In the case of pancreatic cancer patients of the present invention, endothelial cells are the main cellular component in cancer tissue, and the endothelial cells in the tumor microenvironment can support self-renewal and maintenance of cancer-initiating cells through Notch, TGF-β, nitric oxide (NO), sonic hedgehog (SHH), integrin, and Wnt cell signaling pathways.

Since the pancreatic cancer organoids of the present invention sufficiently reflect the interaction between cancer cells and endothelial cells, that is, cross-talk with the vascular niche, they can show the characteristics of cancer-initiating cells (CICs) present in the organism environment, compared to conventional pancreatic cancer organoids, and thus may be very effectively used to study the development of pancreatic cancer, resistance to drugs, and the like. Furthermore, when such organoids are used, the clinical applicability and reliability of the screened drug may be further remarkably increased.

The biological sample in the present invention refers to any substance, biological fluid, tissue or cell obtained or derived from an individual who is a pancreatic cancer patient, and examples thereof include, but are not limited to, blood (including whole blood, leukocytes, peripheral blood mononuclear cells, buffy coat, plasma and serum), sputum, tears, mucus, nasal washes, nasal aspirate, breath, urine, semen, saliva, peritoneal washings, pelvic fluids, cystic fluid, meningeal fluid, amniotic fluid, glandular fluid, pancreatic fluid, lymph fluid, pleural fluid, nipple aspirate, bronchial aspirate, synovial fluid, joint aspirate, organ secretions, cells, cell extract, or cerebrospinal fluid. For the purposes of the present invention, the biological sample may be a tissue or pancreatic cancer cell line isolated from a pancreatic cancer patient, and may be, for example, a tissue isolated from a pancreatic cancer patient, without being limited thereto.

Since the pancreatic cancer organoids of the present invention are obtained without primary culture of cancer cells dissociated from cancer tissue obtained from a patient, genetic modification in cancer cells, which may occur in this process, or loss of phenotypic characteristics in vitro, may be very effectively prevented.

For the purpose of the present invention, the pancreatic cancer may be pancreatic ductal adenocarcinoma, without being limited thereto. In the case of the tissue obtained from a pancreatic ductal adenocarcinoma patient, histological characteristics similar to those of the original cancer tissue can be very effectively maintained even in vitro compared to other types of cancer, even without mutation analysis for confirming the origin of the cancer.

The endothelial cells in step d) of the present invention may be vascular endothelial cells, for example, human umbilical vein endothelial cells (HUVECs), without being limited thereto.

In step d) of the present invention, the pancreatic cancer organoids and the endothelial cells may be mixed together at a ratio of 1:1 to 1:6, for example, 1:4, without being limited thereto. When pancreatic cancer organoids containing endothelial cells are prepared by mixing at a ratio of 1:1 to 1:6 as described above, they can fully reflect the interaction between endothelial cells and pancreatic cancer cells in the tumor microenvironment and can more effectively show the characteristics of cancer-initiating cells.

The conditioned medium in step d) of the present invention refers to a product obtained by culturing cells in a known liquid medium or solid medium and does not contain cells.

In step a) of the present invention, the step of dissociating may be performed using collagenase, for example, collagenase D (collagenase type IV), without being limited thereto. Since the collagenase D has low trypsin activity, cell damage in the process of dissociating tissue into cells may be minimized.

The pancreatic cancer organoids containing endothelial cells according to the present invention may contain cancer-initiating cells. For the purposes of the present invention, the pancreatic cancer organoids enable the self-renewal and maintenance of cell-initiating cells to be supported by interaction with endothelial cells or by substances contained in the culture supernatant of endothelial cells, even when a separate growth factor capable of maintaining cancer-initiating cells is not added.

Step b) of forming organoids in the present invention may be performed by culturing the dissociated sample of step a) in a DMEM/F12 medium further containing at least one selected from the group consisting of antibiotics, glutamine, B27, N-acetyl-L-cysteine, growth factors, gastrin, cell signaling inhibitors, PGE2 (prostaglandin E2), and additives. For the purposes of the present invention, when this medium is used, cells dissociated from tissues can be transformed into cancer organoids very effectively even without primary culture.

The "antibiotic" in the present invention serves to prevent contamination by bacteria, fungi, microplasma, enzymes, and the like in the process of culturing pancreatic cancer organoids, and examples thereof include, but are not limited to, ampicillin, penicillin, streptomycin, spectinomycin, tetracycline, neomycin, penicillin and streptomycin.

The "glutamine" in the present invention is an essential component that provides energy during cell culture, and may be alanyl glutamine or glutamine dipeptide, for example, L-alanyl-L-glutamine (GlutaMAX), without being limited thereto.

The "B27" in the present invention corresponds to a serum-free supplement optimized to help cell growth or viability.

The "growth factor" in the present invention is a protein or steroid hormone capable of stimulating cell growth, proliferation, healing and cell differentiation, and examples thereof include, but are not limited to, Noggin recombinant protein, epidermal growth factor, and fibroblast growth factor 10.

The "cell signaling inhibitors" in the present invention refers to inhibitors functioning to prevent the binding of growth factors to receptors or block the activation of receptors in order to inhibit the activation of signaling pathways inside cells. For the purposes of the present invention, the cell signaling inhibitors may be an AK inhibitor and a p38 MAPK inhibitor, for example, A83-01 (CAS No. 909910-43-6) and SB202190 (CAS No. 152121-30 -7), without being limited thereto.

The "additives" in the present invention may be Wnt3a-conditioned medium, RSPO1-conditioned medium, and nicotinamide, without being limited thereto.

Another embodiment of the present invention provides a pancreatic cancer organoid prepared by the preparation method of the present invention.

Since the pancreatic cancer organoids of the present invention are prepared according to the preparation method of the present invention, they may be used very effectively to study the development of pancreatic cancer, resistance to drugs, and the like. Furthermore, when such organoids are used, the clinical applicability and reliability of the screened drug may be further remarkably increased.

In the pancreatic cancer organoids of the present invention, contents regarding pancreatic cancer, endothelial cells, conditioned medium, ratio, collagenase, etc. are as described above with respect to the method for preparing pancreatic cancer organoids, and thus detailed description thereof will be omitted to avoid excessive complexity of the present specification.

Another embodiment of the present invention provides a method for screening a therapeutic agent for pancreatic cancer.

The method for screening a therapeutic agent for pancreatic cancer according to the present invention comprises steps of: a) treating the pancreatic cancer organoid according to the present invention with a candidate substance; and b) observing cancer cells contained in the pancreatic cancer organoid after treatment with the candidate substance.

Step b) of the screening method of the present invention may comprise, when the size of cancer cells is reduced or maintained or the number of cancer-initiating cells is reduced, selecting the candidate substance as the therapeutic agent for pancreatic cancer.

The "screening" in the present invention means specifically selecting only a substance having a desired specific property from a candidate group consisting of various substances.

The "candidate substance" in the present invention refers to an unknown substance expected to have inhibitory activity against the growth or metastasis of cancer tissue or to induce the death of cancer-initiating cells. Examples of the candidate substance include, but are not limited to, compounds, peptides, proteins, antibodies, and natural extracts.

The candidate substance in the present invention may be obtained through synthetic or natural compound libraries, biological libraries, spatially addressable parallel solid phase or solution phase libraries, or the like.

Advantageous Effects

The pancreatic cancer organoids prepared by the method of the present invention sufficiently reflect the interaction between cancer cells and endothelial cells, that is, cross-talk with the vascular niche, and thus they can show the characteristics of cancer-initiating cells (CICs) present in the organism environment, compared to conventional pancreatic cancer organoids. Accordingly, the clinical applicability and reliability of the screened drug may be further remarkably increased.

(−) cells by fluorescence microscopy according to one example of the present invention.

Figure 8:
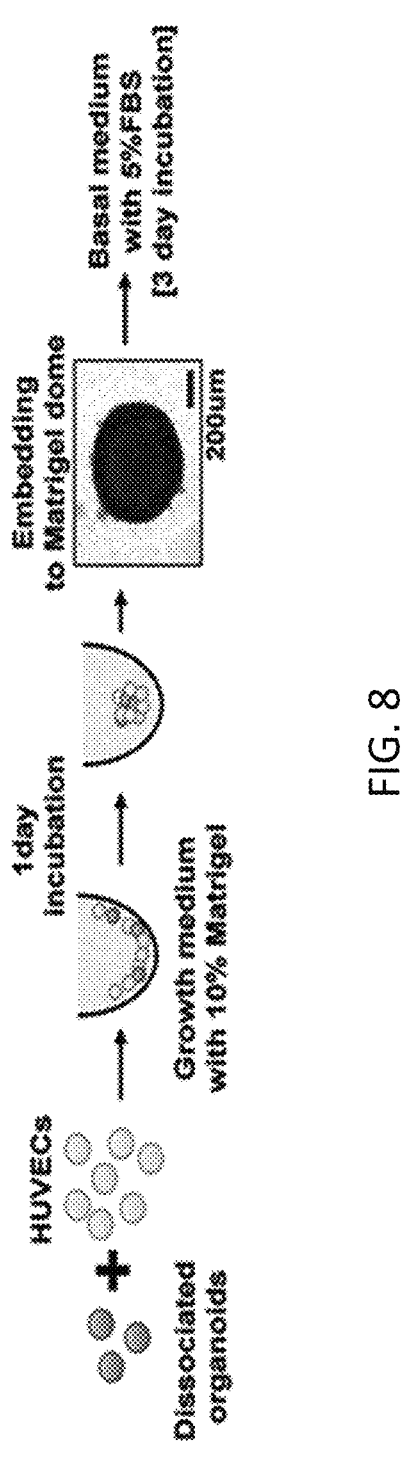

FIG. 8 is a schematic view showing a method of preparing a pancreatic cancer organoid system, which is a pancreatic cancer organoid containing human umbilical vein endothelial cells (HUVECs), according to one example of the present invention.

Figure 9:
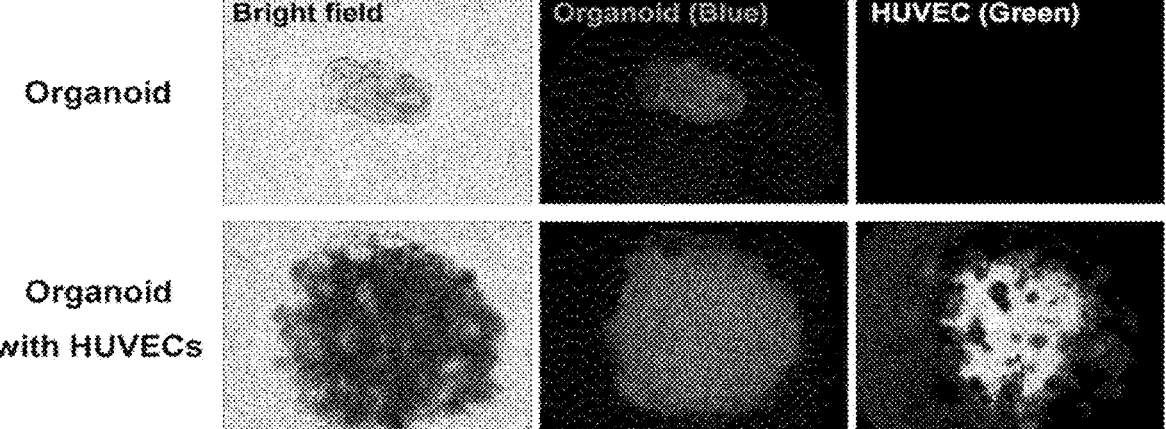

FIG. 9 shows the results of analyzing the morphology of a pancreatic cancer organoid and an organoid system, which is a pancreatic cancer organoid containing HUVECs, by fluorescence microscopy, according to an example of the present invention.

Figure 10:
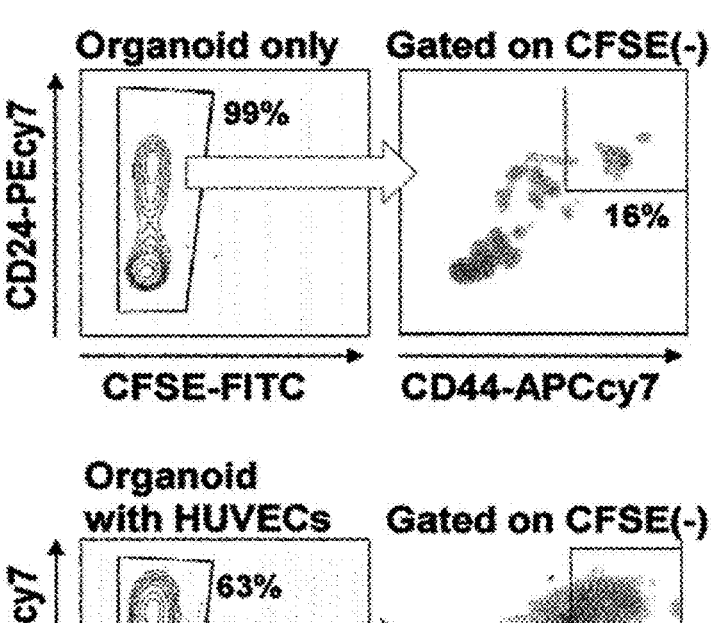

FIG. 10 shows the results of analyzing the cell morphology of cancer-initiating cells in an organoid system, which is a pancreatic cancer organoid containing HUVECs, by flow cytometry, according to one example of the present invention.

Figure 11:
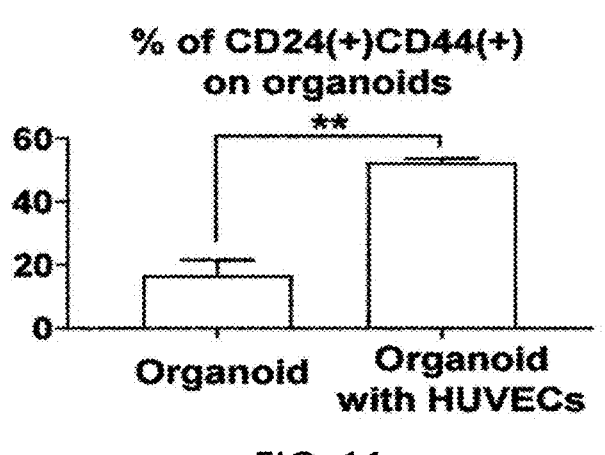

FIG. 11 shows the results of comparing the number of cancer-initiating cells between a pancreatic cancer organoid and a pancreatic cancer organoid system, which is a pancreatic cancer organoid containing HUVECs, according to one example of the present invention.

Figure 12:
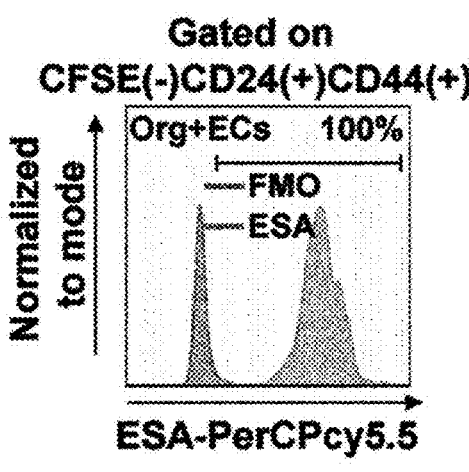

FIG. 12 shows the results of analyzing the cell morphology of cancer-initiating cells in an organoid system, which is a pancreatic cancer organoid containing HUVECs, by flow cytometry, according to one example of the present invention.

Figure 13A:
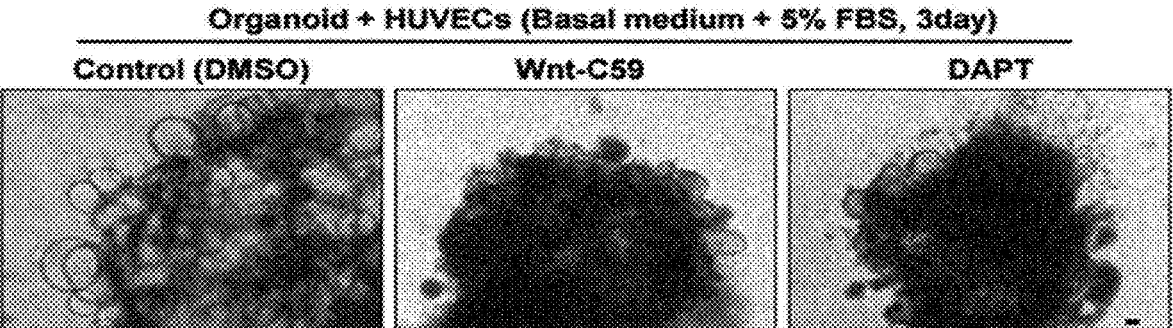
Figure 13B:
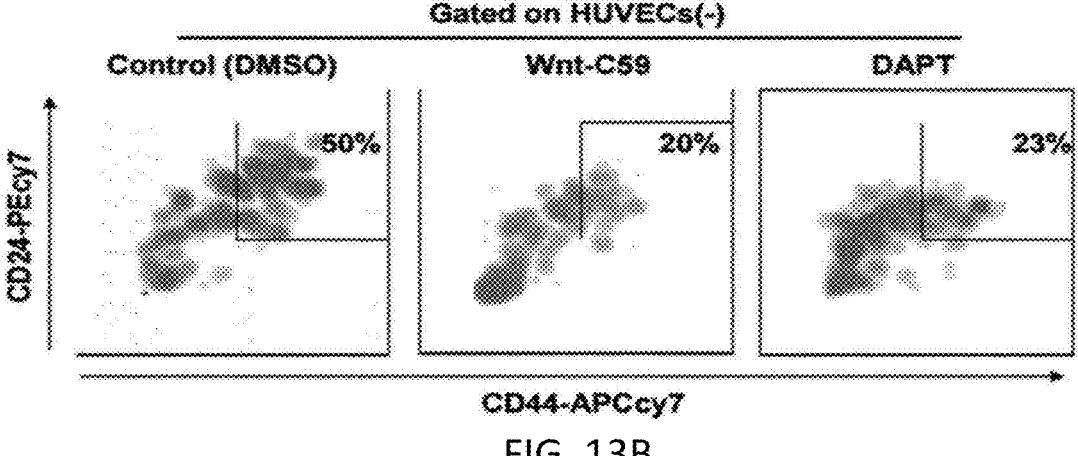

FIGS. 13A and 13B show the results of confirming that the formation of pancreatic cancer organoids containing HUVECs is inhibited upon inhibition of Wnt or Notch cell signaling, by microscopy, and analyzing the phenotype of cancer-initiating cells by flow cytometry, according to one example of the present invention.

Figure 14:
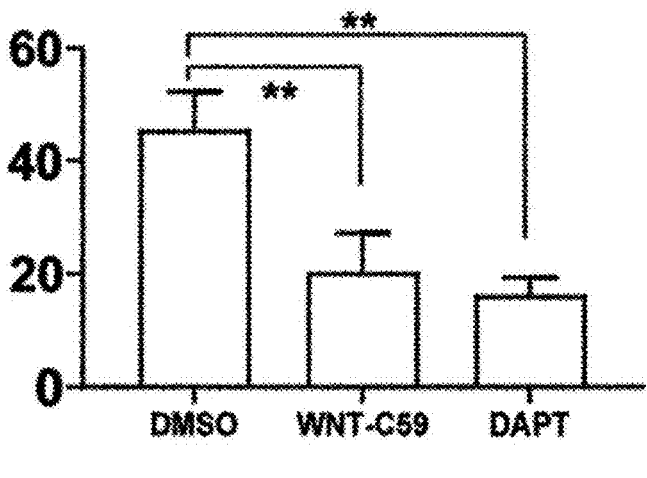

FIG. 14 shows the results of measuring the number of cells having a cancer-initiating cell phenotype in pancreatic cancer organoids containing HUVECs upon inhibition of Wnt or Notch cell signaling, according to one example of the present invention.

Figure 15:
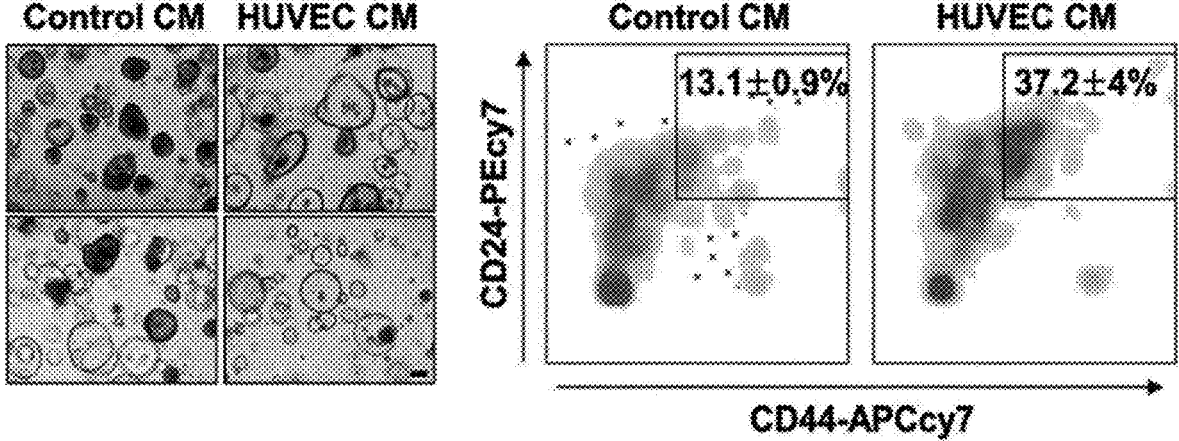

FIG. 15 shows the results of analyzing the cell morphology and phenotype of pancreatic cancer organoids, cultured using a conditioned medium (CM) corresponding to a control cell conditioned medium or a HUVEC conditioned medium, by microscopy and flow cytometry, according to one example of the present invention.

Figure 16:
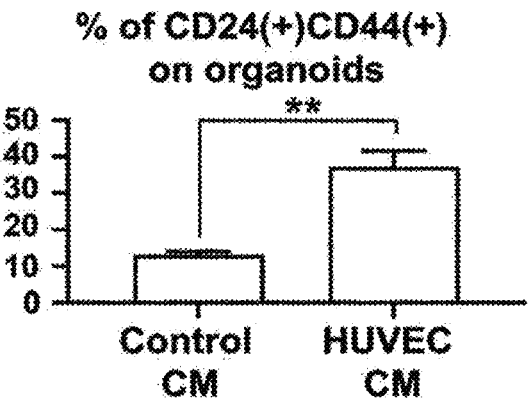

FIG. 16 shows the results of analyzing the percentage of cells having a CD24(+)CD44(+) phenotype in pancreatic cancer organoids, cultured using a conditioned medium (CM) corresponding to a control cell conditioned medium or a HUVEC culture medium, by flow cytometry, according to one example of the present invention.

BEST MODE

One embodiment of the present invention provides a method for preparing pancreatic cancer organoids, the method comprising steps of: a) dissociating a biological sample isolated from a pancreatic cancer patient and immobilizing the dissociated biological sample on Matrigel; b) forming pancreatic cancer organoids by culturing the sample immobilized on Matrigel in step a); c) dissociating the pancreatic cancer organoids formed in step b); and d) co-culturing the dissociated pancreatic cancer organoids with endothelial cells, or adding an endothelial cell conditioned medium to the dissociated pancreatic cancer organoids, followed by culture.

Another embodiment of the present invention provides a pancreatic cancer organoid prepared by the preparation method according to the present invention.

Still another embodiment of the present invention provides a method for screening a therapeutic agent for pancreatic cancer, the method comprising steps of: a) treating the pancreatic cancer organoid of the present invention with a candidate substance; and b) observing cancer cells contained in the pancreatic cancer organoid containing endothelial cells after treatment with the candidate substance.

Mode for Invention

Hereinafter, the present invention will be described in more detail with reference to examples. These examples are only for explaining the present invention in more detail, and it will be apparent to those skilled in the art that the scope of the present invention according to the subject matter of the present invention is not limited by these examples.

Experimental Methods

[Experimental Method 1] Pancreatic Ductal Adenocarcinoma Patient Samples

Pancreatic ductal adenocarcinoma (PDAC) tissues and endoscopic ultrasound-guided fine needle aspiration (EUS-FNA) samples were obtained from Severance Hospital, Yonsei University College of Medicine. All human experiments related to this application were approved by the institutional review board (IRB) of Severance Hospital. According to IRB guidelines, informed consent was obtained from pancreatic cancer patient donors.

[Experimental Method 2] Establishment of Human Pancreatic Cancer Organoid

The tissue samples obtained in Experimental Method 1 were diced, and the diced tissue samples were sufficiently digested by incubation in DMEM (Dulbecco's Modified Eagle's medium) containing 2 mg/mL of collagenase D (Sigma-Aldrich, catalog No. 11088866001) and 10% FBS (fetal bovine serum) for 90 min at 37° C. Next, the digested tissues were washed with DPBS (distilled phosphate buffer saline) containing 10% FBS (fetal bovine serum) and embedded in growth factor reduced (GFR) Matrigel (Corning, catalog No. 356231). Here, for the EUS-FNA (endoscopic ultrasound-guided fine needle aspiration) sample, a small amount of cellular material was collected by centrifugation 400×g for 10 min, and the EUS-FNA sample was lysed with RBC lysis buffer (Qiagen, catalog No. 158904) and washed twice with adDMEM/F12 medium (Thermo Fisher Scientific).

Then, after polymerizing the matrix by incubation in an incubator for 10 min, pancreatic cancer organoid culture medium (medium 1) consisting of adDMEM/F12 supplemented with the components listed in Table 1 below was added and culture was performed until organoids were formed. Next, when organoid formation appeared, the pancreatic cancer organoid culture medium was replaced with a PGE2-free medium (medium 2). After two passages, an experiment was performed to confirm the characteristics of organoids described below.

TABLE 1

| Component | Manufacturer |
|---|---|
| GlutaMAX | Invitrogen |
| Antibiotics (penicillin/streptomycin) | Invitrogen |
| B27 | Invitrogen |
| 1 mM, N-acetyl-L-cystein | Sigma-Aldrich |
| 50% v/v, Wnt3a-conditioned medium | Sigma-Aldrich |
| 10% v/v, RSPO1-conditioned medium | R&D systems |
| 100 ng/ml, Noggin recombinant protein | PeproTech |

TABLE 1-continued

| Component | Manufacturer |
|---|---|
| 50 ng/ml, epidermal growth factor | PeproTech |
| 10 nM, gastrin | Sigma-Aldrich |
| 100 ng/ml, fibroblast growth factor 10 | PeproTech |
| 10 mM, nicotinamide | Sigma-Aldrich |
| 0.5 μM, A83-01 | Tocris |
| 10 μM, SB202190 | Sigma-Aldrich |
| 1 μM, PGE2 | PeproTech |

For passage of the pancreatic cancer organoids, the organoids were disrupted by digestion with TrypLE Express (Invitrogen, catalog No. 12604013), and then washed with adDMEM/F12 medium to remove trypsin. Finally, pancreatic cancer organoid fragments were embedded in GFR Matrigel, and 10 μM of Y-27632 (Tocris) was additionally added to the pancreatic cancer organoid culture medium (medium 1) described in Table 1. Hereinafter, organoids prepared in this way will be referred to as human pancreatic cancer organoids.

[Experimental Method 3] Cell Line Culture Method

HUVECs (human umbilical vein endothelial cells) were dispensed on 1% gelatin-coated culture dishes and cultured in EBM-2 Basal Medium (Lonza, catalog No. CC-3156) supplemented with 1×EGM-2MV SingleQuots Supplement Pack (catalog No. CC-4147). In this case, the medium was replaced every 2 or 3 days.

In addition, human pancreatic ductal adenocarcinoma (PDAC) cell lines (AsPC1, Mia PACA2 and PANC1) were obtained from the Korean Cell Line Bank. The AsPC1 cell line was cultured in RPMI1640 containing 10% FBS, and Mia PACA2 and PANC1 were cultured in DMEM containing 10% FBS.

Figure 4:
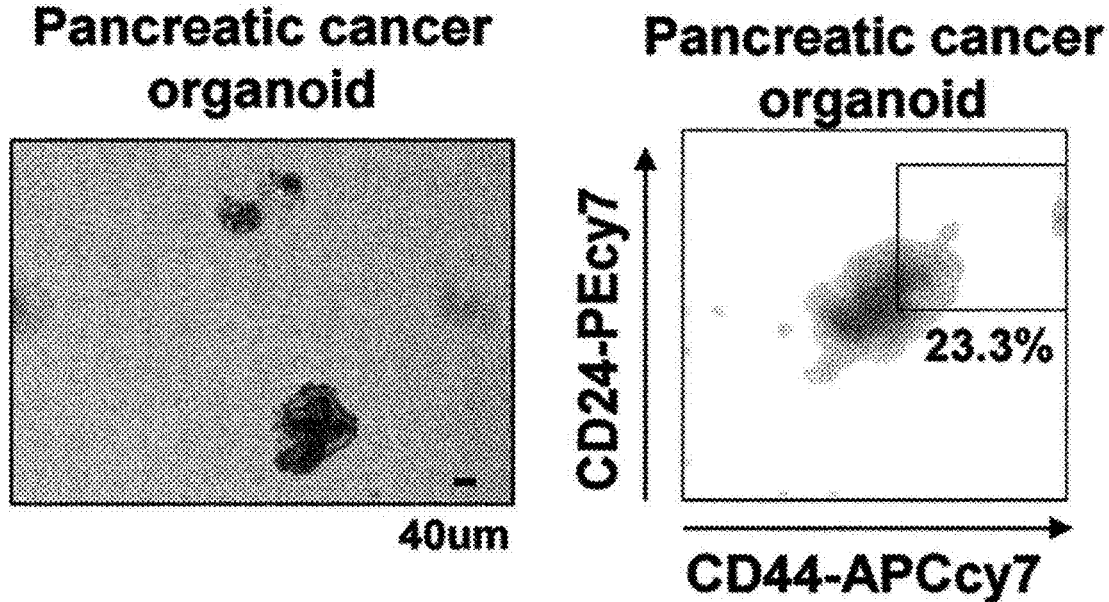
FIG. 4 shows the results of analyzing the cell morphology and phenotype of cancer-initiating cells in a pancreatic cancer organoid when growth factors were excluded, by microscopy or flow cytometry, according to one example of the present invention.

[Experimental Method 4] Method for Co-Culture of Pancreatic Cancer Organoids with HUVECs As shown in FIG. 4, a pancreatic cancer organoid containing HUVECs (hereinafter referred to as "human-derived pancreatic cancer organoid system") was established by co-culture of human-derived pancreatic cancer organoids with HUVECs. Specifically, the pancreatic cancer organoids prepared in Experimental Method 2 were dissociated using TrypLE Express and then stained using CellTracker Blue CMAC dye, and HUVECs were stained carboxyfluorescein succinimidyl ester (CFSE; Thermo) according to the manufacturer's protocol. The human pancreatic cancer organoids and the HUVECs were mixed together at a ratio of 1:4 ($5\times10^5$ cells:$2\times10^6$ cells). Next, the cell mixture was added to round-bottom ultra-low attachment plates (Corning) and medium 1 containing 10% Matrigel was added thereto. Then, the plates were centrifuged at 100×g for 3 min and incubated for 1 day to form aggregates.

The aggregates were embedded in the GFR Matrigel. Upon sufficient solidification, the aggregates were washed with basal medium and then cultured for 3 days in adDMEM/F12 containing 5% FBS and GlutaMAX, thereby establishing a first human pancreatic cancer organoid system.

Here, for experiments for confirming inhibition of the Wnt and Notch cell signaling pathways, 100 nM of Wnt-C59 or 200 μM of DAPT, which is cell signaling inhibitors, was added when embedding the aggregates in GFR Matrigel, followed by culture for 3 days. In addition, in order to analyze the cell phenotype, the aggregates of the human pancreatic cancer organoid system were sufficiently dissociated using TrypLE Express and then analyzed by flow cytometry described in [5-1] below.

[Experimental Method 5] Culture of Human Pancreatic Cancer Organoids Using HUVEC Conditioned Medium HUVECs were dispensed in GM-2MV and then cultured until they reached 95% confluence. The HUVECs were washed twice, and the medium was replaced with AdD-MEM/F12 containing 5% fetal bovine serum and Gluta-MAX, followed by culture in an incubator at 37° C. for 3 days.

Meanwhile, for a control, AdDMEM/F12 containing 5% fetal bovine serum and GlutaMAX on a plate without cells (HUVECs) was placed in an incubator at 37° C. for 3 days.

The obtained conditioned medium was centrifuged at 4° C., and the supernatant was collected and filtered through a 0.22 μm filter to obtain a conditioned medium corresponding to the supernatant. For Wnt-C59 and DAPT pre-treatment HUVEC conditioned medium (CM), HUVEC cells were cultured for 1 day after treatment with Wnt-C59 and DAPT. After the cells were washed twice, the medium was replaced with AdDMEM/F12 containing 5% FBS and GlutaMAX, followed by culture for 3 days. Next, a conditioned medium corresponding to the supernatant was obtained in the same manner as described above.

A second human-derived pancreatic cancer organoid system was prepared by adding the obtained conditioned medium to the pancreatic cancer organoid prepared in Experimental Method 2.

[Experimental Method 6] Measurement, Staining and Analysis Methods

[6-1] Flow Cytometry

For cell surface staining, cells dissociated from the aggregates of Experimental Method 4 were collected in fluorescence-activated cell sorting (FACS) buffer (dPBS, Gibco) containing 1% FBS and 0.1% BSA (MP bio) and then blocked using an Fc receptor blocker (Miltenyi Biotec). Next, the cells were stained using CD44-APCcy7 (BioLegend), CD24-Pecy7, and EpCAM-PerCPcy5.5. Then, flow cytometry was performed using LSR II, and the cells were analyzed using FlowJo and DIVA software.

[6-2] Immunofluorescence Staining

The human pancreatic cancer organoids or the human or cell-derived pancreatic cancer organoid systems were fixed in PBS (1% paraformaldehyde with 0.1% glutaraldehyde) for 10 min and then washed at least three times with PBS containing 10 mM $NaBH_4$. All samples were blocked with 1% BSA (bovine serum albumin) at room temperature for 1 hour. Organoids or pancreatic cancer organoid systems stained with CD44 antibody were washed three times with PBS.

Thereafter, the human pancreatic cancer organoids or the human or cell-derived pancreatic cancer organoid systems were incubated with a secondary antibody and DAPI (4,6-diamidino-2-phenylindole) for 1 hour, washed three times with PBS, and then observed using a Zeiss LSM710 laser scan confocal local microscope.

[6-3] Statistical Analysis

Experimental results are presented as the mean ±SEM values. Statistical comparisons for two different samples were performed using the Mann-Whitney U test. To compare multiple samples, statistical significance was assessed using Dunnett's multiple comparisons test. A P value <0.05 was considered statistically significant. Statistical tests were performed using the statistical package SPSS version 25 (SPSS Inc., Chicago, IL) and GraphPad Prism 8.

[Experimental Method 7] Wnt Activity Assay

HEK 293 STF cells (ATCC, CRL-3249) were seeded into white 96-well plates and cultured in DMEM containing 10%

FBS and 200 μg/ml of G-418. Then, the cells were incubated with 50% conditioned medium and control medium for 48 hours.

Luciferase signal was measured using Bright-Glo Luciferase Assay System (Promega) according to the manufacturer's instructions.

Experimental Results

[Experimental results 1] Confirmation of Enrichment of Cancer-Initiating Cells

[1-1] Analysis of Phenotype and Appearance of Human Pancreatic Cancer Organoids

The phenotypes corresponding to CD24(+)CD44(+) and CD24(+)CD44(+)ESA(+)in the human pancreatic cancer organoids of Experimental Example 2 were analyzed, and the results are shown in FIGS. 1A, 1B, 2 and 3.

Figure 1A:
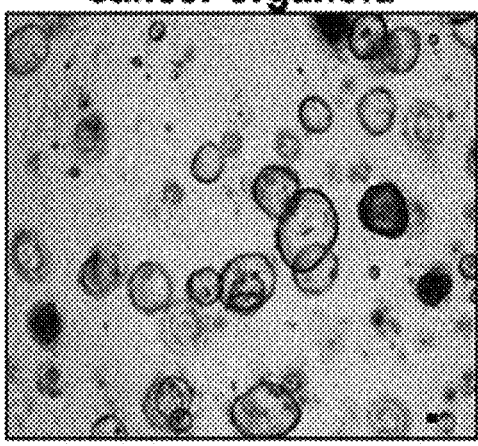
FIGS. 1A and 1B show the results of analyzing the appearance and cellular phenotype of pancreatic cancer organoids by microscopy or flow cytometry according to one example of the present invention.
Figure 1B:
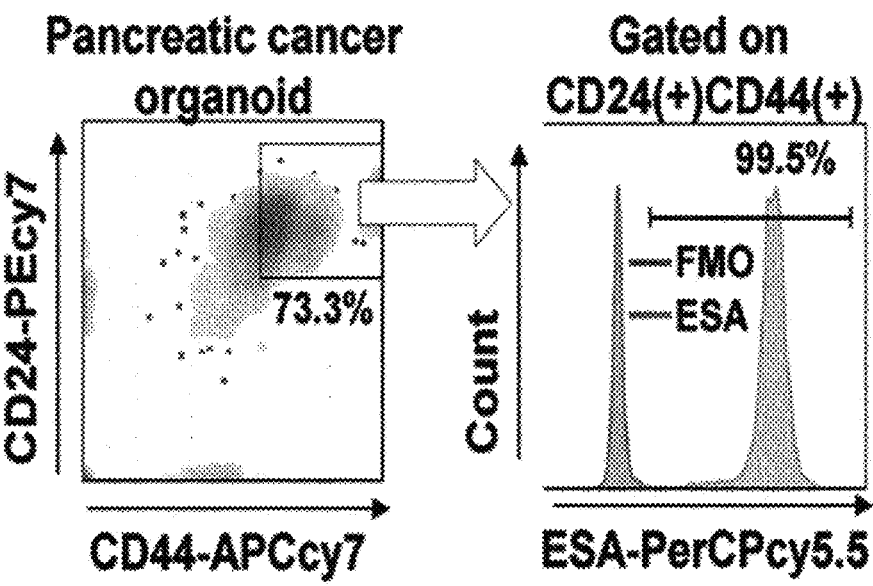

As shown in FIGS. 1A and 1B, in both microscopy (A) and flow cytometry (B), cells having a CD24(+)CD44(+) phenotype in human pancreatic cancer organoids accounted for 73.3%, and cells having an ESA(+) phenotype among the cells having a CD24(+)CD44(+) phenotype accounted for 99.5%.

Figure 2:
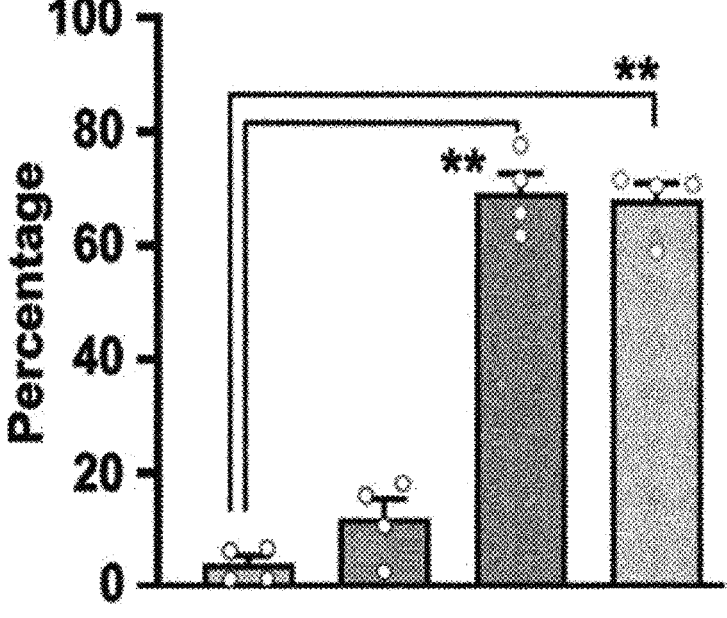
FIG. 2 is a graph showing the percentage of cells having each phenotype in pancreatic cancer organoids, analyzed by flow cytometry according to one example of the present invention.
Figure 2:
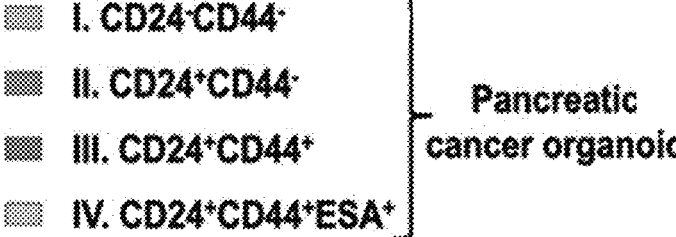

As shown in FIG. 2, it was confirmed that cancer-initiating cells (CICs) corresponding to CD24(+) CD44(+) in human pancreatic cancer organoids totaled 69.2 ±3.5%, and 99.5 ±0.3% of CD24(+)CD44(+) cells were ESA (+) cells.

Figure 3:
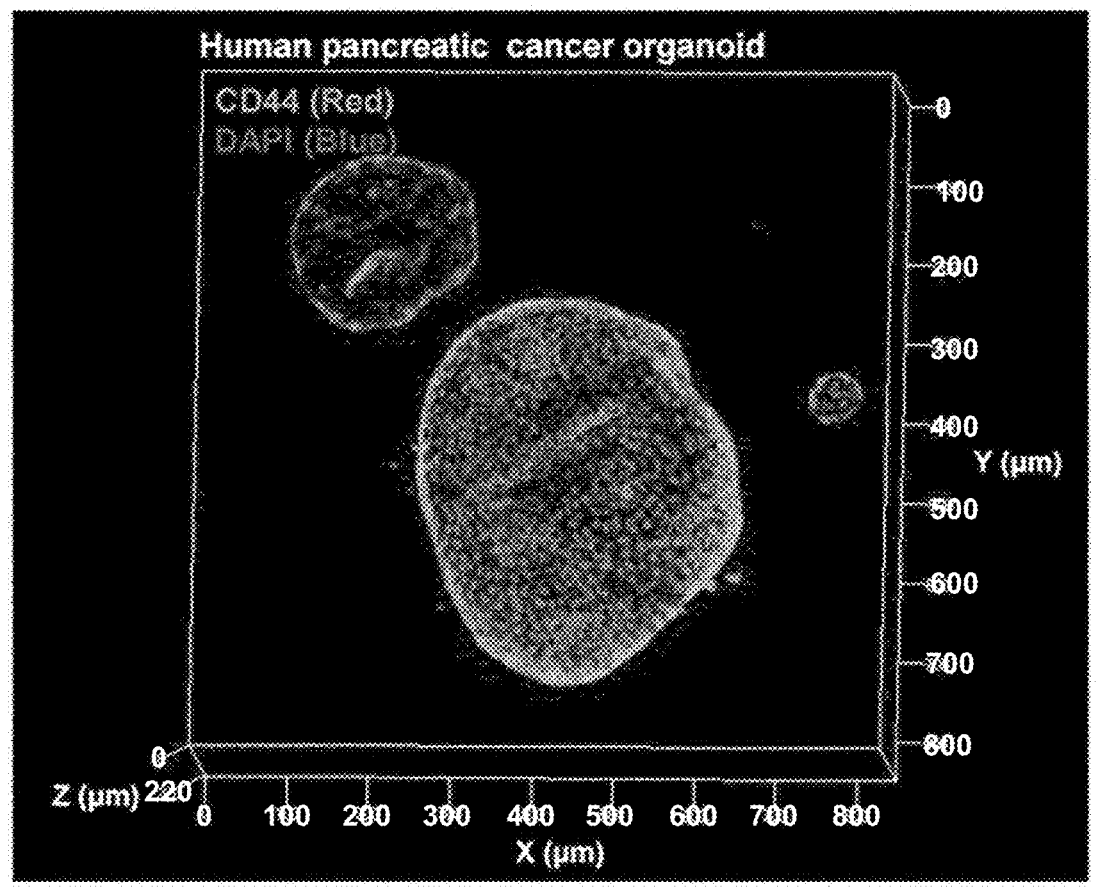
FIG. 3 shows the results of observing the three-dimensional structure of a pancreatic cancer organoid by a confocal microscope according to one example of the present invention.

As shown in FIG. 3, it was confirmed that CD44 was highly expressed in human pancreatic cancer organoids, and the cells constituting the organoids were organized into a three-dimensional circle (lumen structure) with an empty center.

From these results, it can be seen that CD24(+)CD44(+) and CD24(+)CD44(+)ESA(+) cells were enriched at a higher level than CD24(−)CD44(−) cells in human pancreatic cancer organoids.

[1-2] Confirmation of Maintenance of Cancer-Initiating Cells in Pancreatic Cancer Organoids To determine whether cancer-initiating cells can be maintained by artificial stem cell support factors, the human pancreatic cancer organoids of Experimental Method 2 were cultured in basal medium (adDMEM/F12 medium containing 5% FBS and GlutaMAX), and the cell number and phenotype were observed, and the results are shown in FIG. 4.

As shown in FIG. 4, the number of cancer-initiating cells decreased when cultured in basal medium for 3 days.

From these results, it can be seen that cancer-initiating cells in pancreatic cancer organoids can be expanded by factors such as Wnt, EGF and FGF.

[Experimental Results 2] Assessment of Organoid Formation Potential

The organoid formation potential of CD24(+)CD44(−) or CD24(−/low)CD44(−) cells sorted from human pancreatic cancer organoids was assessed.

Figure 5:
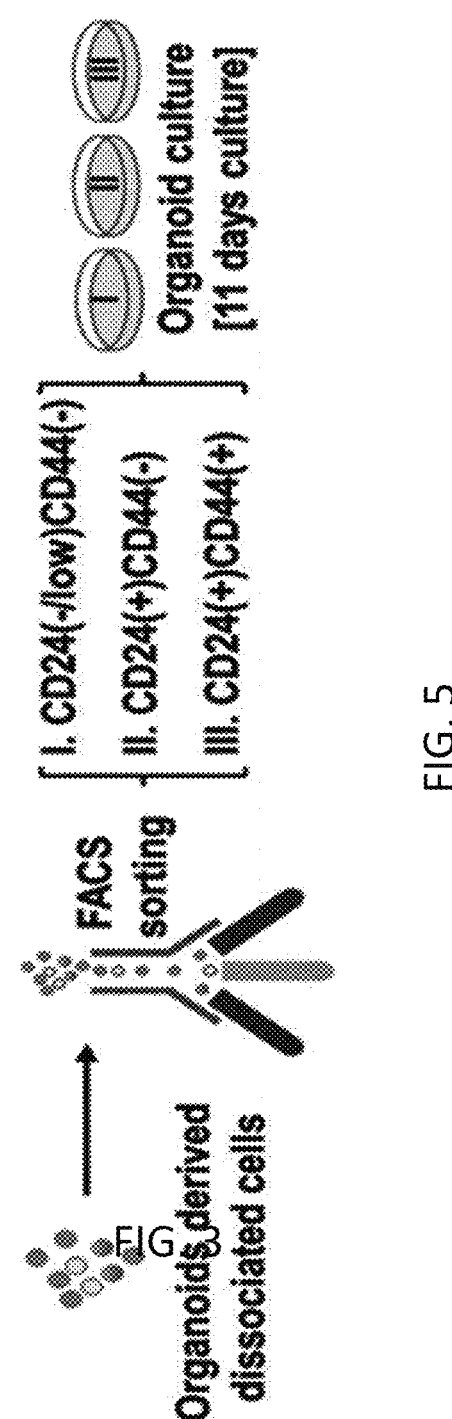
FIG. 5 is a schematic view showing a method of preparing an organoid system by sorting cells present in human pancreatic cancer organoids into cell lines with different phenotypes, followed by 11 days of culture, according to one example of the present invention.

Specifically, as shown in FIG. 5, CD24(−low)CD44(−), CD24(+)CD44(−) and CD24(+)CD44(+) cells were sorted from the human pancreatic cancer organoids by flow cytometry (FACS) and cultured using medium 1 and medium 2 for 11 days. Then, flow cytometry and fluorescence microscopy were performed, and the results are shown in FIGS. 6 and 7.

Figure 6:
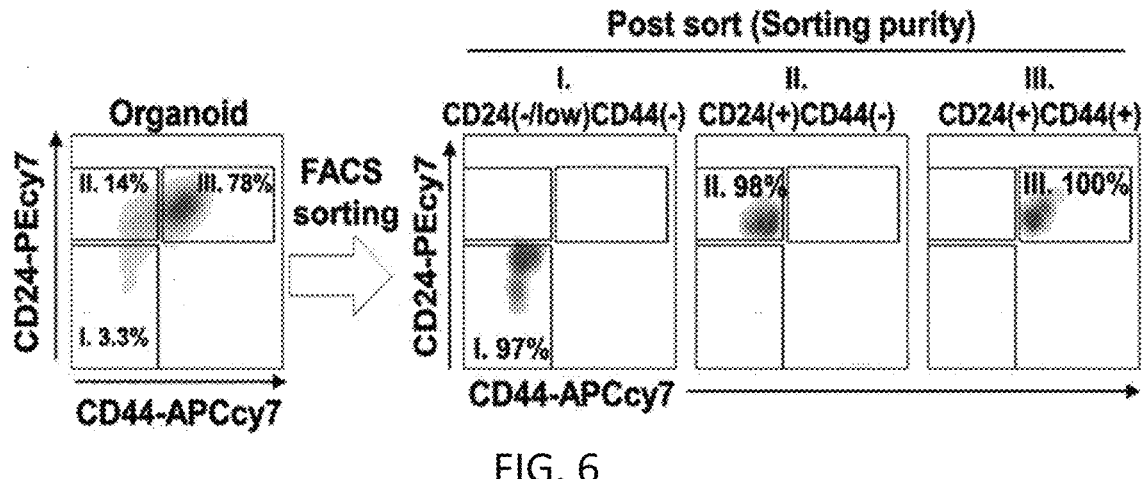
FIG. 6 shows the results of analyzing the organoid formation potential of CD24(+)CD44(−) or CD24(−/low)CD44(−) cells, sorted from human pancreatic cancer organoids, by flow cytometry, according to one example of the present invention.
Figure 7:
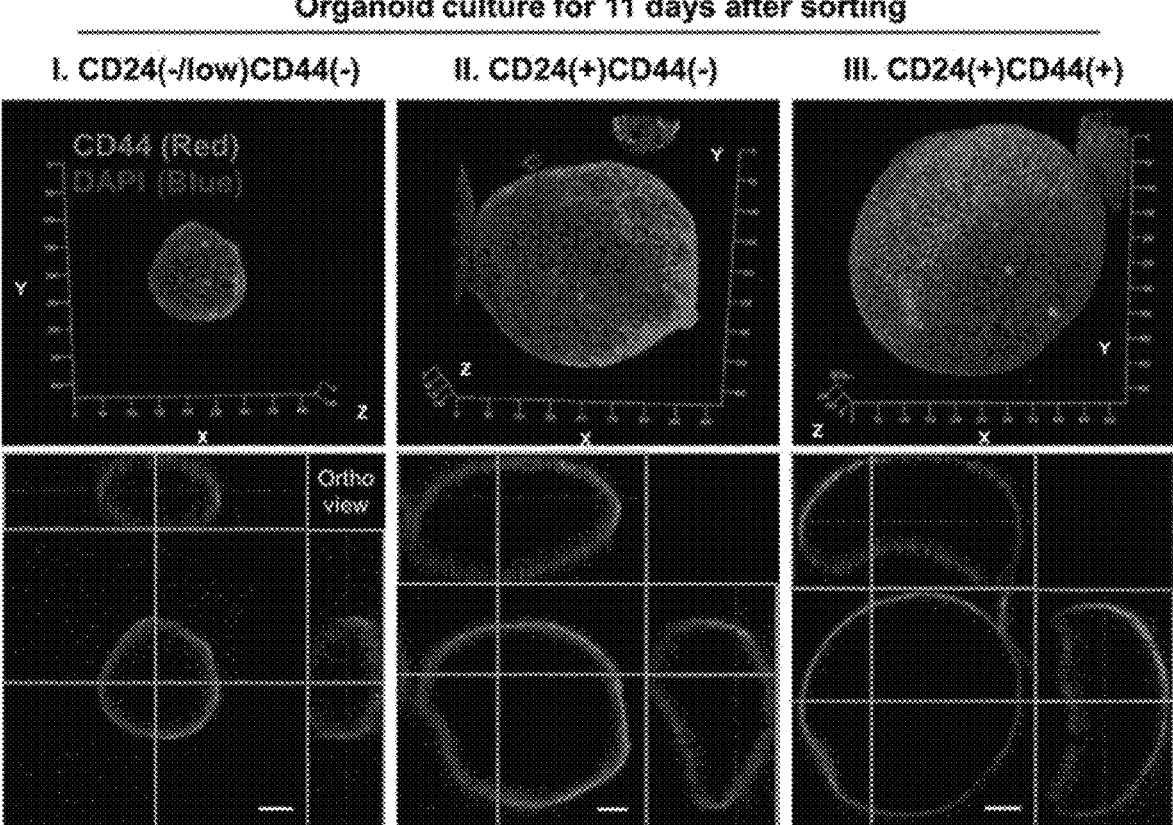
FIG. 7 shows the results of analyzing the organoid formation potential of CD24(+)CD44(−) or CD24(−/low)CD44

As shown in FIGS. 6 and 7, organoids prepared by culturing CD24(+)CD44(−) and CD24(−/low)CD44(−) also expressed CD44 (FIG. 6), and CD24(+)CD44(−) and CD24 (−/low)CD44(−) cells, as well as CD24(+)CD44(+) cells, were re-organized into a circle and center-empty lumen structure (FIG. 7).

From these results, it can be seen that the organoid culture medium including Wnt, EGF and FGF can induce expansion of CD24(+)CD44(+) cancer-initiating cells and CD24(+)CD44(+)ESA(+) cancer-initiating cells, and CD24(+)CD44(−) and CD24(−/low)CD44(−) cells can be reprogrammed to CD44(+) cancer-initiating cells.

[Experimental Results 3] Confirmation of Interaction Between Endothelial Cells and Cancer-Initiating Cells In order to confirm whether self-renewal and maintenance of cancer-initiating cells are supported by endothelial cells, the first human pancreatic cancer organoid system and human-derived pancreatic cancer organoids in Experimental Example 4 were cultured in an environment excluding growth factors. Then, cell morphology and phenotype were observed, and the results are shown in FIGS. 9 to 12.

As shown in FIG. 9, it was confirmed that the size of the organoid itself in the first human pancreatic cancer organoid system was significantly larger than the human pancreatic cancer organoid.

In addition, as shown in FIGS. 10 to 12, it was confirmed that the number of CD24(+)CD44(+) corresponding to the phenotype of cancer-initiating cells in the first human-derived pancreatic cancer organoid system was larger than that in the human pancreatic cancer organoids (FIGS. 10 and FIG. 11), and that 100% of cells having such a phenotype were ESA-positive cells (FIG. 12).

[Experimental Results 4] Analysis of Cell Signaling Involved in Interaction Between Endothelial Cells and Cancer-Initiating Cells The organoid formation process upon inhibition of cell signaling in the first human pancreatic cancer organoid system was examined, and the results are shown in FIGS. 13A, 13B and 14.

As shown in FIGS. 13A, 13B and 14, when Wnt or Notch cell signaling was inhibited, organoid formation in the organoid system was inhibited (FIG. 13A).

Furthermore, it was confirmed that the number of cancer-initiating cells in the organoid system was also significantly reduced (FIGS. 13B and 14).

From these results, it can be seen that the cancer-initiating cells present in the pancreatic cancer organoid system self-renew and are maintained by interaction with endothelial cells, and that this phenomenon occurs due to Wnt and Notch cell signaling.

[Experimental results 5] Characterization of Human Organoid System Using HUVECs Supernatant To evaluate the roles of secreted proteins, such as Wnt or Notch ligands from endothelial cells in the maintenance of cancer-initiating cells, pancreatic cancer organoids were cultured in AdDMEM/F12 with the HUVEC conditioned medium (CM) containing 5% fetal bovine serum, the morphology thereof was analyzed by microscopy, and the cell phenotype was analyzed by flow cytometry. The results are shown in FIGS. 15 and 16. Here, as described in Experimental Method 5 above, as a control, conditioned medium alone without cells (HUVECs) was incubated in an incubator at 37° C.

As shown in FIGS. 15 and 16, it was confirmed that CD44+ cells having a cancer-initiating cell phenotype significantly increased when cultured using HUVEC conditioned medium (CM) compared to when cultured using control conditioned medium (CM).

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereto.

INDUSTRIAL APPLICABILITY

The pancreatic cancer organoids prepared by the method of the present invention sufficiently reflect the interaction between cancer cells and endothelial cells, that is, cross-talk with the vascular niche, and thus they can show the characteristics of cancer-initiating cells (CICs) present in the organism environment, compared to conventional cancer organoids. Accordingly, the clinical applicability and reliability of the screened drug may be further remarkably increased.

The invention claimed is:

1. A method for preparing pancreatic cancer organoids containing cancer-initiating cells (CICs), comprising steps of:
   a) dissociating a biological sample isolated from a pancreatic cancer patient and immobilizing the dissociated biological sample on a growth factor reduced basement membrane matrix;
   b) forming pancreatic cancer organoids by culturing the sample immobilized on the growth factor reduced basement membrane matrix in step a);
   c) dissociating the pancreatic cancer organoids formed in step b); and
   d) co-culturing the dissociated pancreatic cancer organoids with vascular endothelial cells, or adding a vascular endothelial cell conditioned medium to the dissociated pancreatic cancer organoids, followed by culture in an environment excluding growth factors.

2. The method according to claim 1, wherein the co-culturing in step d) comprises mixing the pancreatic cancer organoids and the endothelial cells at a ratio of 1:1 to 1:6 and culturing the mixture.

3. The method according to claim 1, wherein the dissociating in step a) is performed using collagenase.

4. The method according to claim 1, wherein the pancreatic cancer is pancreatic ductal adenocarcinoma.

5. The method according to claim 1, wherein step b) of forming the organoids is performed by culturing the dissociated sample of step a) in a DMEM/F12 medium further containing at least one selected from the group consisting of antibiotics, glutamine, B27, N-acetyl-L-cysteine, gastrin, cell signaling inhibitors, and PGE2 (prostaglandin E2).

6. A method according to claim 1 , further comprising the steps of:
   e treating the pancreatic cancer organoid of step d) with a candidate substance; and
   f observing cancer cells contained in the pancreatic cancer organoid containing endothelial cells after treatment with the candidate substance.

7. The method according to claim 6, wherein the pancreatic cancer is pancreatic ductal adenocarcinoma.

* * * * *